United States Patent
Ghazizadeh

(10) Patent No.: US 9,672,623 B2
(45) Date of Patent: Jun. 6, 2017

(54) IMAGE CALIBRATION

(71) Applicant: Pixameter Corp., Los Gatos, CA (US)

(72) Inventor: Mansoor Ghazizadeh, Los Gatos, CA (US)

(73) Assignee: Pixameter Corp., Los Gatos, CA (US)

( * ) Notice: Subject to any disclaimer, the term of this patent is extended or adjusted under 35 U.S.C. 154(b) by 0 days.

(21) Appl. No.: 13/791,987

(22) Filed: Mar. 9, 2013

(65) Prior Publication Data

US 2014/0098243 A1 Apr. 10, 2014

Related U.S. Application Data

(63) Continuation-in-part of application No. 13/720,260, filed on Dec. 19, 2012, now Pat. No. 9,410,827.

(60) Provisional application No. 61/795,013, filed on Oct. 9, 2012.

(51) Int. Cl.
  *G06T 7/80* (2017.01)
  *G06T 7/00* (2017.01)
(52) U.S. Cl.
  CPC ............... *G06T 7/0018* (2013.01); *G06T 7/80* (2017.01); *G06T 2207/30204* (2013.01)
(58) Field of Classification Search
  CPC .... G06F 3/038; G06F 3/04817; G06F 3/0488; G06F 17/00; G06F 1/1632; G06F 1/1686; G06F 3/048; H04M 2250/12; H04M 1/22; H04M 1/72563; H04M 2250/10; H04M 1/72522; H04M 1/72547; H04M 1/7255; H04M 1/72552; G06T 7/80; G06T 2207/30204

USPC ............ 455/456.1, 67.11, 550.1, 423, 67.14, 455/226.1, 418, 425, 456.2, 456.3, 456.5
See application file for complete search history.

(56) References Cited

U.S. PATENT DOCUMENTS

| | | | |
|---|---|---|---|
| 6,118,845 A * | 9/2000 | Simon | A61B 6/583 378/207 |
| 7,248,284 B2 | 7/2007 | Pierce | |
| 2002/0067855 A1* | 6/2002 | Chiu | G06T 7/0018 382/199 |
| 2002/0145769 A1* | 10/2002 | Pollard | 358/504 |
| 2004/0027456 A1 | 2/2004 | Pierce | |
| 2004/0150726 A1* | 8/2004 | Gallagher | 348/222.1 |
| 2004/0215413 A1* | 10/2004 | Weldum | H04N 1/32128 702/85 |
| 2005/0225813 A1* | 10/2005 | Lai et al. | 358/504 |
| 2007/0036454 A1* | 2/2007 | Crucs | 382/254 |
| 2009/0033785 A1* | 2/2009 | Fujinawa et al. | 348/333.01 |
| 2009/0252371 A1* | 10/2009 | Rao | 382/100 |

(Continued)

OTHER PUBLICATIONS

Tape Measure! Jollo Apps, located at https://play.google.com/store/apps/details?id=com.tape.measure&hl=en, Aug. 19, 2019.

(Continued)

*Primary Examiner* — Sonji Johnson
(74) *Attorney, Agent, or Firm* — Chernoff Vilhauer McClung & Stenzel, LLP

(57) ABSTRACT

A digital image is captured. The captured digital image includes a calibration pattern. The calibration pattern includes displayed information about the calibration pattern. The displayed information is read to obtain calibration information about the captured digital image. A new image is generated. The calibration information is stored with the new image.

4 Claims, 15 Drawing Sheets

(56) References Cited

U.S. PATENT DOCUMENTS

| | | | |
|---|---|---|---|
| 2010/0033612 A1* | 2/2010 | Hsia et al. | 348/308 |
| 2010/0067738 A1* | 3/2010 | Petricoin, Jr. | 382/103 |
| 2010/0259608 A1* | 10/2010 | Knuuttila | 348/135 |
| 2012/0122529 A1* | 5/2012 | Lyons | 463/1 |
| 2012/0122558 A1* | 5/2012 | Lyons et al. | 463/25 |
| 2012/0196382 A1* | 8/2012 | Chan et al. | 436/501 |
| 2013/0188841 A1* | 7/2013 | Pollock | 382/108 |
| 2013/0259403 A1* | 10/2013 | Osinusi | 382/294 |
| 2013/0278779 A1* | 10/2013 | Hong | 348/187 |
| 2014/0056495 A1* | 2/2014 | Janssens | 382/128 |

OTHER PUBLICATIONS

Digital Targets from Photovision, located at www.photovisionvideo.com/digital-targets/, 2012.

* cited by examiner

IMAGE CALIBRATION

BACKGROUND

Smart mobile devices such as smartphones, feature phones, tablet, e-readers, media players, and so on, combine capabilities from multiple single function devices into a single device. Typically such smart mobile devices include various combinations of the capability found in devices such as a cell phone, a programmable computer, a camera, a media player and a portable Internet access device.

Many smart mobile devices contain one or more digital cameras that allow a user of the smart mobile device to take high resolution and high fidelity digital pictures. For example, some smart mobile devices include two cameras, one in the front of the smart mobile device and one in the back of the smart mobile device. Currently, typical smartphones are able to capture images with a digital resolution of, for example, five to eight megapixels. The trend is to increase the digital resolution of cameras on smart mobile devices. Some cameras for smart mobile digital devices allow for 3D image capture.

Cameras in smart mobile devices are especially handy to capture still or short video clips of memorable events and allow easy storage and sharing with others. A captured digital image typically is represented as a two dimensional matrix of dots, also called pixels.

DETAILED DESCRIPTION

Figure 1:
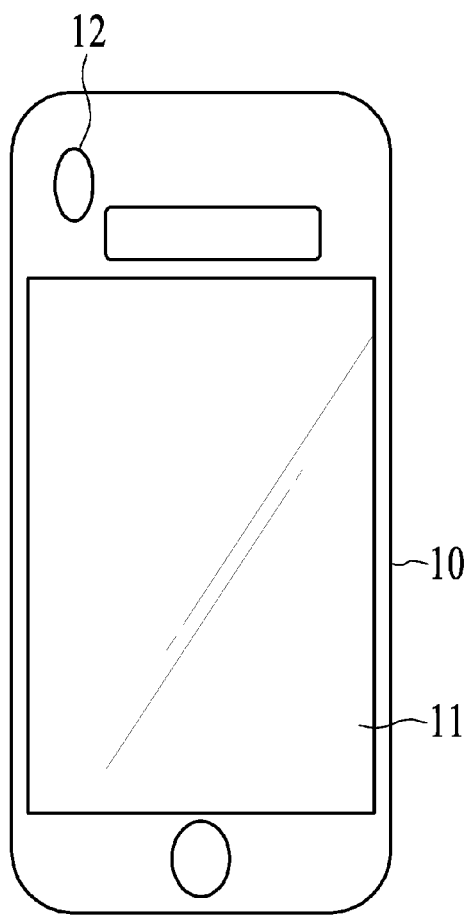
FIG. 1 and FIG. 2 show the front and back, respectively, of a smart mobile device, in accordance with an implementation.
Figure 2:
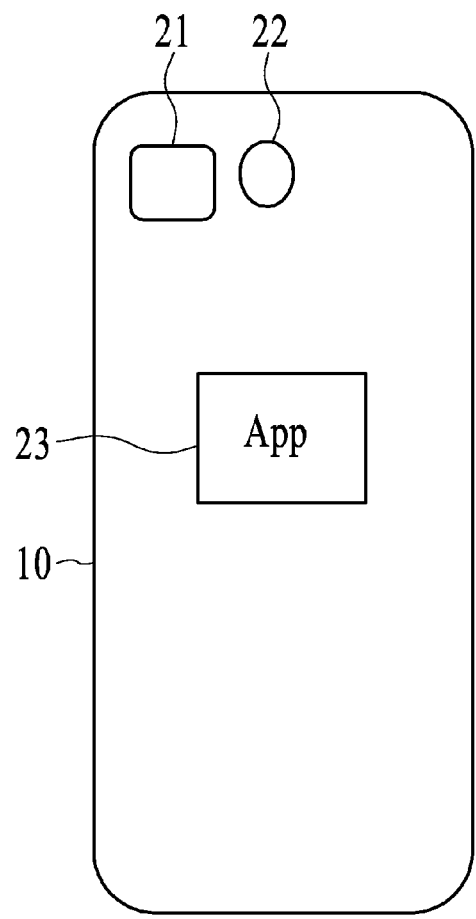

FIG. 1 and FIG. 2 show the front and back, respectively, of a smart mobile device 10. For example, smart mobile device 10 includes a front facing camera 12, and a touch sensitive display 11, as shown in FIG. 1. Smart mobile device 10 also includes, for example, a back facing camera 22 and a back facing flash 21, as shown in FIG. 2. For example smart mobile device 10 is a smart phone, a tablet, an e-reader, a media player, a digital camera or any other portable device that includes a camera and has processing capability sufficient to run a software application that performs measurements based on a calibration pattern. In FIG. 2, app 23 represents a software application, stored in smart mobile device 10, that performs measurements based on a calibration pattern, as described further below.

If calibrated appropriately, images captured by smart mobile device 10 can be used for measuring object size in three dimensions, for measuring a distance between objects and for measuring color and brightness level of objects in a captured image. For example, as described further herein, inclusion of one or more calibration patterns within an image captured by smart mobile device 10 allows for appropriate calibration. In order to facilitate making measurements, the calibration pattern is placed within a focus plane of a camera that captures the digital image. Placement within the focus plane allows for calibrated measurements of other objects in the digital image.

Figure 3:
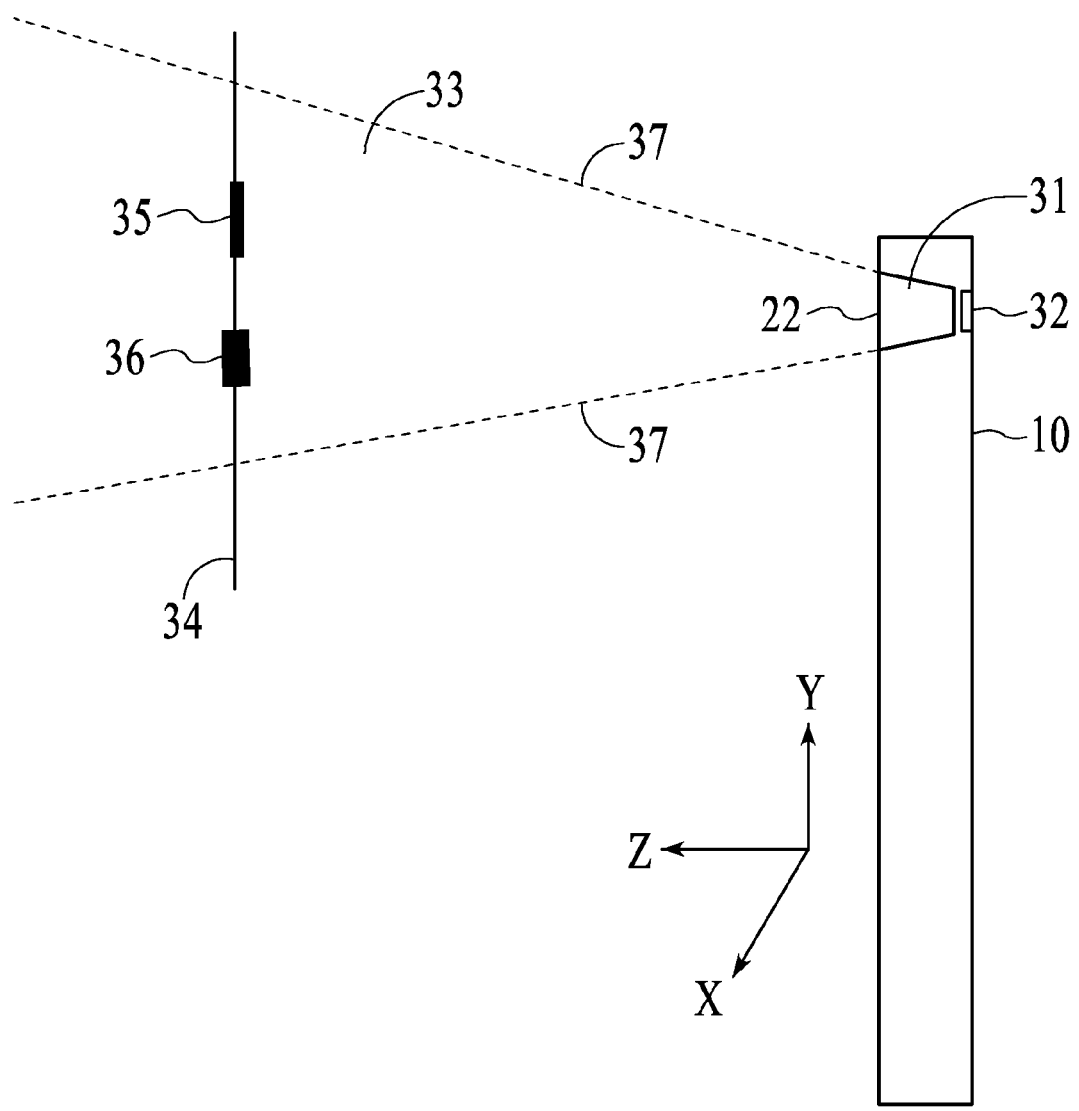
FIG. 3 shows a smart mobile device used to make a calibrated measurement in accordance with an implementation.

FIG. 3 shows a smart mobile device 10 used to make a calibrated measurement. In FIG. 3, back facing camera 22 is shown to include a camera lens 31 and a camera sensor 32. Dotted lines 37 define a field of view 33 for back facing camera 22. An object of measurement 36 is located on a focus plane 34, as shown in FIG. 3. A calibration target 35 is also shown located on focus plane 34.

Focus plane 34 of back facing camera 22 is in a parallel plane to the plane on which camera sensor 32 resides. The distance of focus plane from camera 22 is determined by focus of camera lens 31 of camera 22. Typically, when capturing an image for the purpose of dimension measurements, a camera is best placed parallel with a focus plane (e.g., an X-Y plane) in which measurements will occur. When the focus plane is an X-Y plane, measurements on objects close to the focus plane (e.g., in which a location on the Z axis is close to the X-Y plane) will typically have higher accuracy than measurements made on objects farther from the focus plane (e.g., in which a location on the Z axis is at a greater distance to the X-Y plane). Therefore, it is typically best, where possible, to focus the camera lens on the intended object of measurement and to include a calibration pattern within the focus plane of the camera lens.

A calibration pattern includes one or more known predetermined sub-patterns that have known or knowable characteristics. Including such a calibration pattern in a captured digital image will indicate information about other pixels in the captured digital image. For example, the indicated information obtained from the calibration pattern may include actual dimensions of geometric shapes in the calibration pattern. This can be used to calculate, for example, actual dimension of sizes represented by each pixel within a captured digital image.

Knowing the actual dimension of sizes represented by each pixel within a captured digital image allows for making measurements of dimensional information. A measurement of dimensional information can be any measurement that takes into account information about dimensions. For example, a measurement of dimensional information can be a measurement of one or more of the following: distance between points, length, width, area, bounding box location and size, centroid, perimeter length, number of holes, form factor (ratio of area to the square of perimeter), elongation, moments, best-fitting ellipse, ratio of best-fitting ellipse axes, orientation, roundness, convexity related, convex area, minimum bounding box location, size and orientation, feret diameters at different angles, convexity (ratio of convex perimeter to raw perimeter), solidity (ratio of net area to convex area), perimeter related, perimeter points (blob's boundary and holes), filled area, sorting and selecting blobs based on any calculated feature, and user selection of group of features to calculate.

The indicated information obtained from the calibration pattern may also include, for example, brightness information for grey levels for objects and color information for objects in the calibration pattern. And so on. This can be used to calculate brightness and color information, etc., of other objects within the captured digital image. For a discussion of use of calibration targets in digital photography, see United States Patent Application 2004/0027456 A1 published Feb. 12, 2004.

Figure 4:
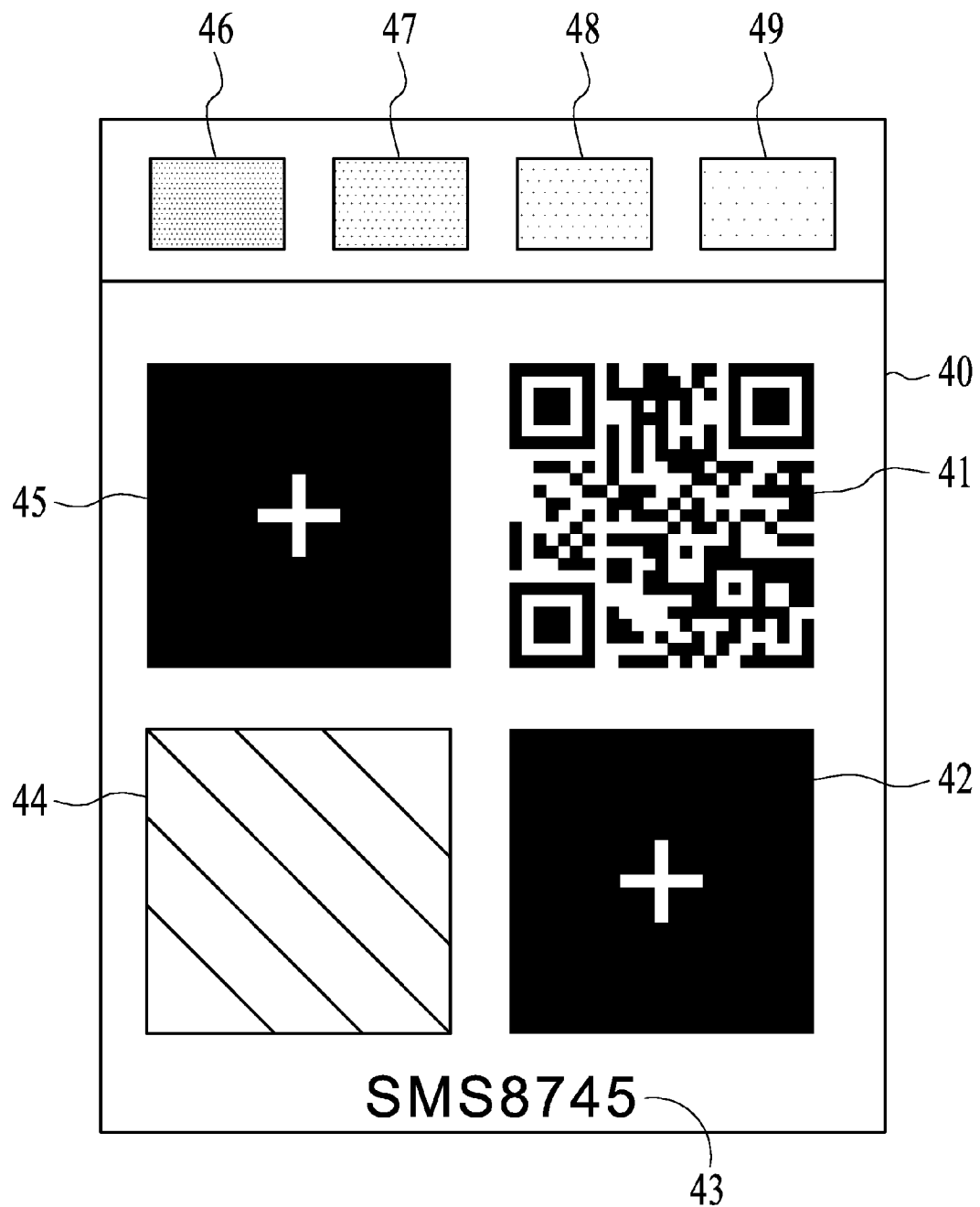
FIG. 4 shows an example of a calibration pattern useful when a smart mobile device makes a calibrated measurement in accordance with an implementation.

FIG. 4 shows an example of a calibration pattern 40 that appears on calibration target 35. Calibration pattern 40 can include, for example, one or a plurality of various calibration sections used for calibration and can also include encoded or otherwise obtainable information that can be recognized by smart mobile device 10. An example of a calibration section within calibration pattern 40 is a geographic pattern 42 that has known or knowable physical dimensions. A high gradient pattern 44 can be used by smart mobile device 10 to sharpen image focus. A geographic pattern 45 is another geographic pattern with known physical dimensions that can be used for dimensional measurements. A red area 46, a blue area 47, a green area 48 and a gray area 49 are colorimetery and brightness calibration patterns that can be used by smart mobile device 10 to calibrate color and brightness for a captured image and/or to calibrate smart mobile device 10.

An identification indicia 43 is visually readable by a user. For example, identification number 43 is a serial number or any other type of number or other identifying indicia that identifies calibration pattern 40. For example, app 23 can check for identifying indicia 43 in order to use the identifying indicia to obtain information about calibration pattern 40. For example, different software applications running on smart mobile device 10 may require different calibration patterns. Each unique calibration pattern can be identified, for example, with an identifying indicia. Information for a particular calibration patterned associated with identifying indicia can be stored locally within smart mobile phone 10 or remotely, for example, in a server accessible by smart mobile phone 10 through the Internet. The information for a calibration pattern can be, for example, dimensional measurements from geometric patterns within the calibration pattern, brightness or color values for entities within the calibration pattern, a specification of the layout of the calibration pattern, a specification for a covering case or other entity on which the calibration pattern is embedded or attached and so on. The information can also include, for example, specifications pertaining to smart mobile device 10, such as packaging specifications and camera specifications.

A two-dimensional bar code 41 is a quick response (QR) code or similar code. Two-dimensional bar code 41 can include the identifying indicia for the calibration pattern thus allowing smart mobile device 10 to identify the calibration pattern in a captured image and access from local or remote storage information about the calibration pattern. Alternatively, or in addition, two-dimensional bar code 41 contains additional information about the calibration pattern. For example, two-dimensional bar code 41, in addition or instead of the identifying indicia for the calibration pattern, contains specific information about actual measurements for sections of the calibration pattern information, information about where the calibration is expected to be located (e.g., on a covering case for mobile device 10) and other information that, for example, may be useful to app 23 when performing measurements. App 23 will capture the information by decoding two-dimensional bar code 41 when two-dimensional bar code 41 is within a captured image. Alternative to two-dimensional bar code 41, calibration pattern 40 can use other means to encode information such as a one dimensional bar code or another information encoding scheme.

A particular calibration pattern can be registered with app 23 so that app 23 assumes that the registered calibration pattern in an image is the registered calibration pattern. This registration information allows app 23 operating within smart mobile device 10 to access information about the calibration target from local or remote memory, without having to read configuration information or the identifying indicia directly from calibration target 23.

When the calibration pattern includes an identifying indicia, whether encoded in a two-dimensional bar code or otherwise readable by mobile device 10, the identifying indicia can be used to check to see if app 23 is configured to be used with that calibration pattern. When app 23 checks the identifying indicia and determines smart mobile device 10 is configured to use the calibration pattern, the user of smart mobile device 10 is given, for example, an opportunity to register smart mobile device 10 to be configured to use the calibration pattern. For example, such registration might require a fee. Once registered, smart mobile device 10 will be able to access information about the calibration pattern. The information can be accessed, for example, from internal memory within smart mobile device 10 or from some external memory source.

A captured digital image that includes calibration pattern 40 in the focus plane allows for calibrated measurements, such as two-dimensional measurements of all objects within the focus plane of calibration pattern 40. Additionally, calibration pattern 40 can then be removed and another digital image captured without the presence of calibration pattern 40. As long as no other changes are made to the camera set-up, measurements can be made on the newly captured image based on calibration information obtained from the originally captured image.

It is also possible to measure distances extending perpendicular (e.g., in the Z dimension). For example, the distance between smart mobile device 10 and an object where calibration pattern 40 resides can be determined by a comparison of pixel sizes in a digital image that includes calibration pattern 40 with the actual size of a known element within calibration pattern 40 while taking into account any magnification performed by camera lens 32.

In order to use smart mobile device 10 as a measuring device, it would be helpful to keep a calibration pattern handy to that could be included in an image captured by smart mobile device 10. This is accomplished, for example, by integrated the calibration pattern into a case for smart mobile device 10.

Figure 5:
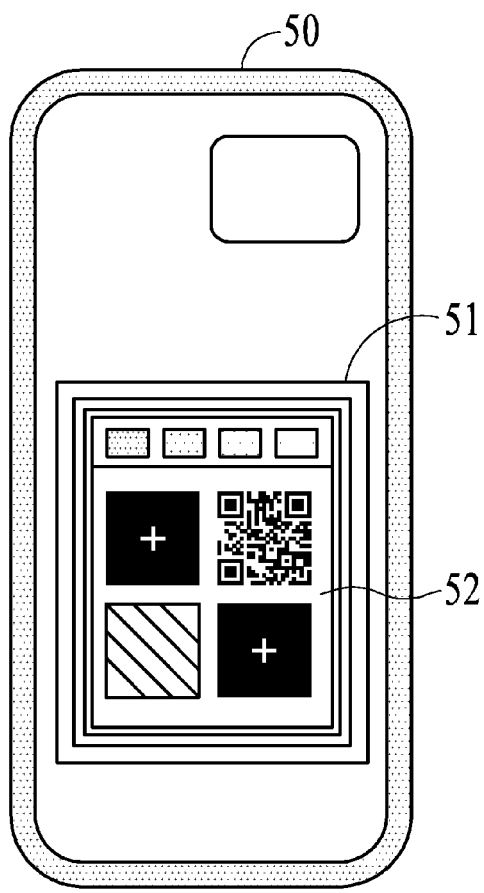
FIG. 5 and FIG. 6 show, respectively, a front view and a back view of a case for a smart mobile device with imprinted calibration patterns useful when a smart mobile device makes a calibrated measurement in accordance with an implementation.
Figure 6:
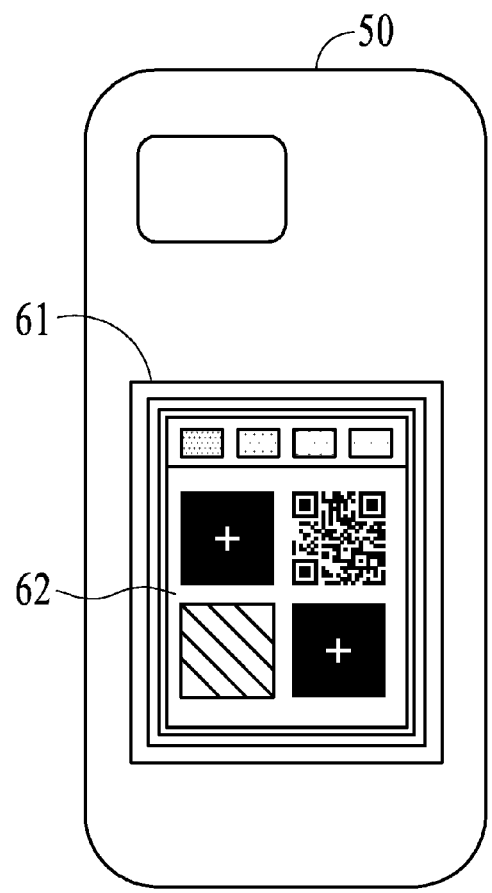

FIG. 5 and FIG. 6 show, respectively, a front view and a back view of a case 50 for smart mobile device 10. FIG. 5 shows a calibration pattern 52 included on case 50. For example, calibration pattern 52 is imprinted within a cavity 51 on the front of case 50. Including calibration pattern 52 within cavity 51 helps to protect calibration pattern 52 from being eroded through friction when placing smart mobile device 10 into case 50 and removing smart mobile device 10 from case 50.

FIG. 6 shows a calibration pattern 62 imprinted within a cavity 61 on the back of case 50. Including calibration pattern 62 within cavity 61 helps to protect calibration pattern 62 from being eroded through friction as case 50 interacts with its environment while protecting smart mobile telephone 10 from damage.

For example, case 50 is a full outerbox skin case, a four-sided skin case, a three-sided skin case, a perimeter bumper case, a holster case, or any other kind of case designed to protect mobile device 10. Case 50 is composed of, for example, hard material such as plastic or metal, or is composed of softer material such as leather or cloth composed of natural or synthetic material. For example, sides of case 50 are constructed to allow case 50 to be stood up on a flat surface without tipping, allowing convenient viewing of calibration pattern 52 and calibration pattern 62.

For example, the calibration pattern can be included on case 50 in various ways. For example, the calibration pattern can be imprinted on case 50 at manufacturing time. Alternately, the calibration pattern can be included on case 50 by, after manufacturing, adhering a label containing the calibration pattern onto case 50 or by any other means which results in calibration pattern being visible on case 50.

A benefit of including a calibration pattern on case 50 is that case 50 can be carried with mobile device 10 and is used to protect mobile device in addition to providing a ready source for the calibration pattern. Case 50 can be easily detached from smart mobile device 10 without affecting functionality of mobile device 10.

Figure 7:
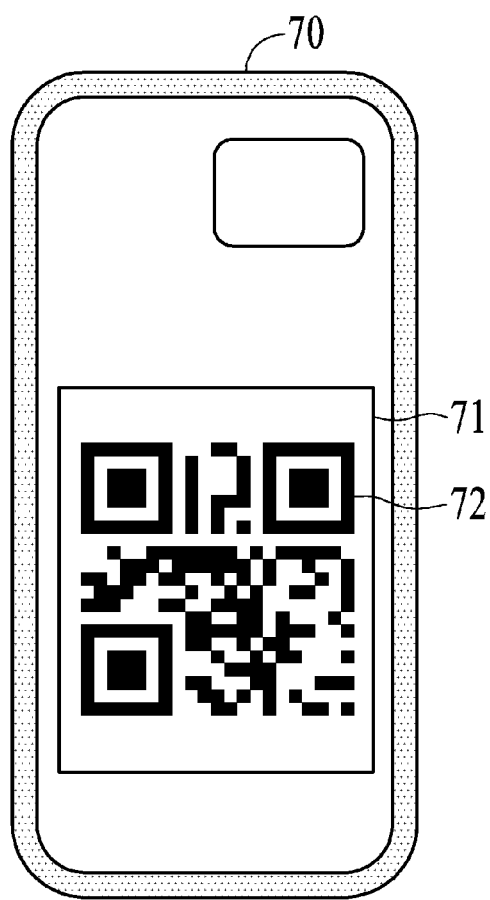
FIG. 7 and FIG. 8 show, respectively, a front view and a back view of a case for a smart mobile device with alternative imprinted calibration patterns useful when a smart mobile device makes a calibrated measurement in accordance with an implementation.
Figure 8:
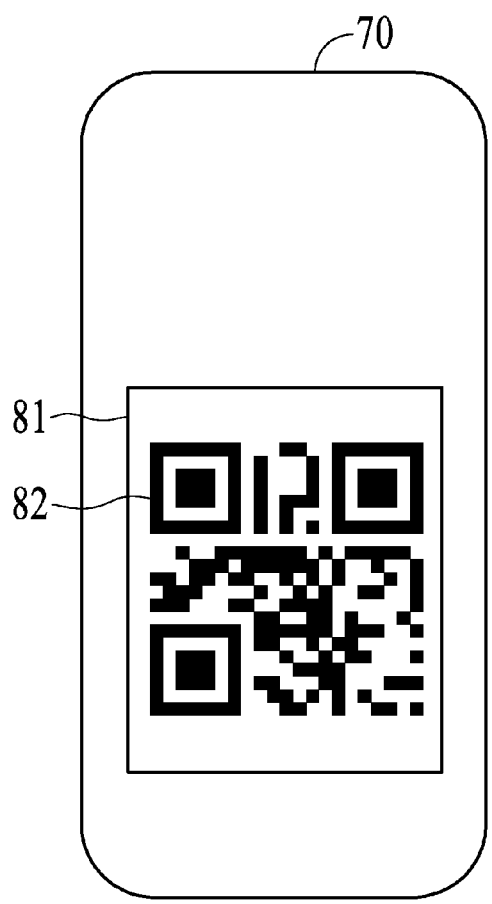

FIG. 7 and FIG. 8 show, respectively, a front view and a back view of a case 70 for smart mobile device 10. FIG. 7 shows a calibration pattern 72 imprinted within a cavity 71 on the front of case 70. Calibration pattern 72 is composed, for example, entirely of a two-dimensional bar code, such as a QR pattern. Including calibration pattern 72 within cavity 71 helps to protect calibration pattern 72 from being eroded through friction when placing smart mobile device 10 into case 70 and removing smart mobile device 10 from case 70.

FIG. 8 shows a calibration pattern 82 imprinted within a cavity 81 on the front of case 70. Calibration pattern 82 is composed, for example, entirely of a two-dimensional bar code, such as a QR pattern. Including calibration pattern 82 within cavity 81 helps to protect calibration pattern 82 from being eroded through friction as case 70 interacts with its environment while protecting smart mobile telephone 10 from damage.

Figure 9:
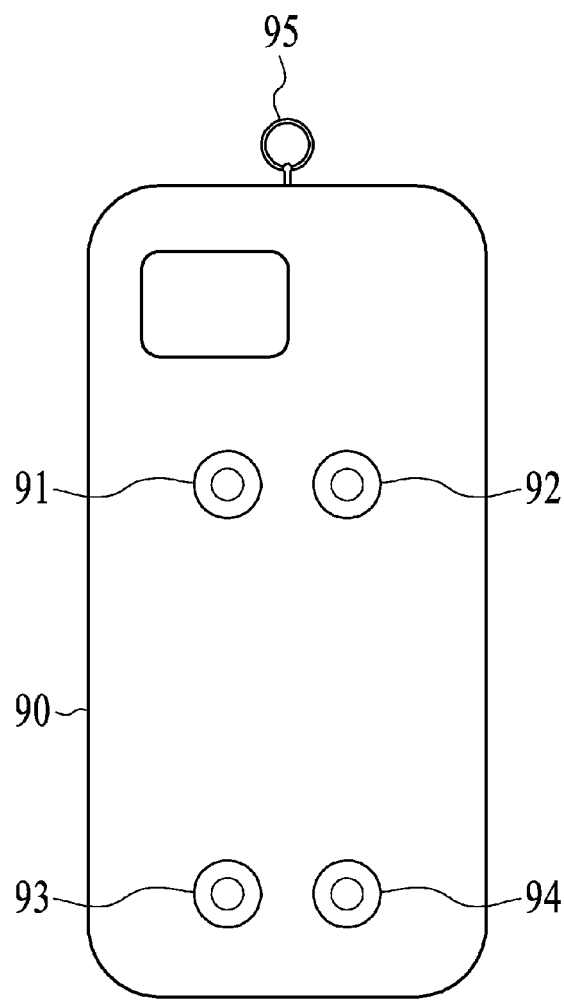
FIG. 9 and FIG. 10 show, respectively, a back view and a side view of a case for a smart mobile device with suction cups and a foldable pin useful when a smart mobile device makes a calibrated measurement in accordance with an implementation.
Figure 10:
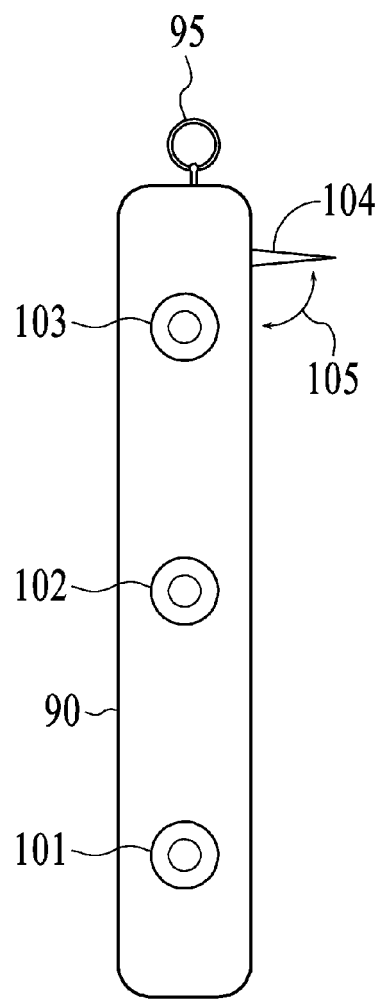

For example, the two-dimensional bar code includes some or all calibration patterns geometries required for, for example, dimensional, brightness/grey level and colorimetery measurements. The two-dimensional bar code thus acts as a calibration pattern. The benefit of using the two-dimensional bar code as a calibration pattern is that the two-dimensional bar code take up much or all of the space available for a calibration pattern and thus can be a sized two-dimensional bar code that can be easier detected within a captured image within a larger field of view FIG. 9 and FIG. 10 show, respectively, a back view and a side view of a case 90 for smart mobile device 10. Case 90 has been outfitted with various appurtenances for allowing case 90 to be mounted on a focus plane when making measurements. For example, FIG. 9 shows a suction cup 91, a suction cup 92, a suction cup 93 and a suction cup 94 embedded on back of case 90. Suction cup 91, suction cup 92, suction cup 93 and suction cup 94 can be used to temporarily adhere the back of case 90 to a hard smooth surface such as metal or glass.

A foldable ring 95 can be used to hang case 90 to a pin, nail, hook and so on. Foldable ring 95 can also be used for hanging by a string, strand, thread, cord, etc.

FIG. 10 additionally shows a suction cup 101, a suction cup 102 and a suction cup 103, embedded on a side of case 90. Suction cup 101, suction cup 102 and suction cup 103 can be used to temporarily adhere the side of case 90 to a smooth surface.

A foldable pin 104 allows case 90 to be attached to soft material, like drywall, and cloth. The foldable design allows for foldable pin 104 to be in an embedded cavity while not in use.

Figure 11:
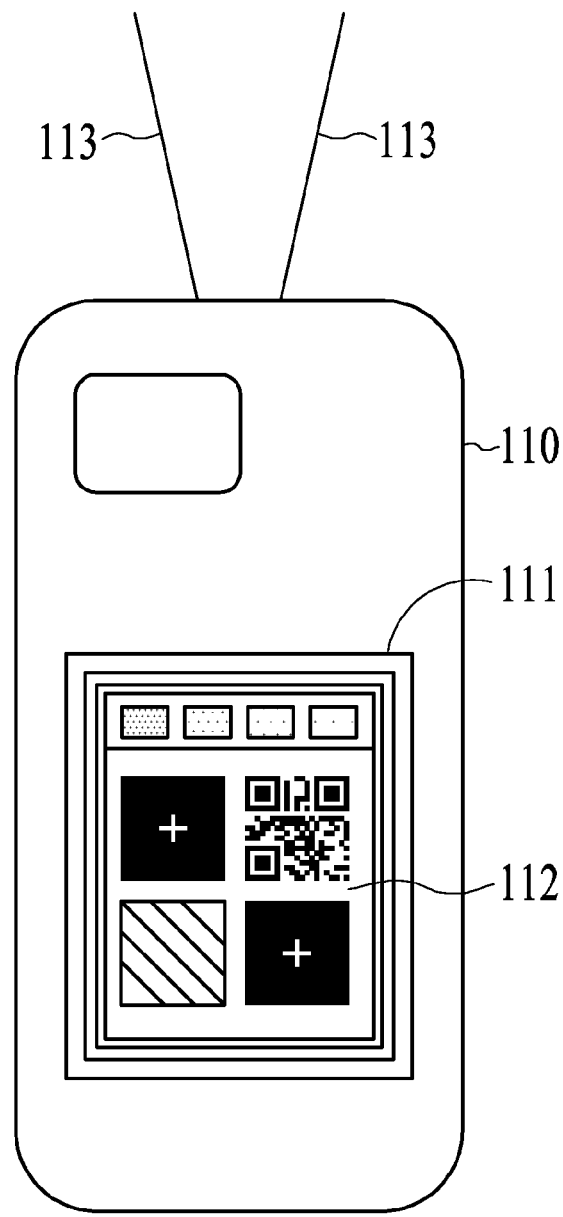
FIG. 11 and FIG. 12 show, respectively, a front view and a top view of a case for a smart mobile device to which a hanging string may be attached so as to be useful when a smart mobile device makes a calibrated measurement in accordance with an implementation.
Figure 12:
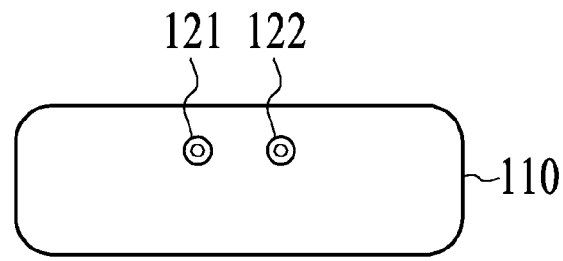

FIG. 11 and FIG. 12 show, respectively, a front view and a top view of a case 110 for smart mobile device 10. FIG. 11 shows a hanging string 113 attached to case 110. Hanging string 113 allows case 110 to be suspended at a desired location when a calibration pattern 112 within an indentation 111 of case 110 is to be used as part of a calibrated measurement performed by mobile device 10. FIG. 12 shows a hang hole 121 and a hang hole 122 located on top of case 110. For example, hanging string 113 is placed through hang hole 121 and hang hole 122 to attach hanging string 113 to case 110.

Figure 13:
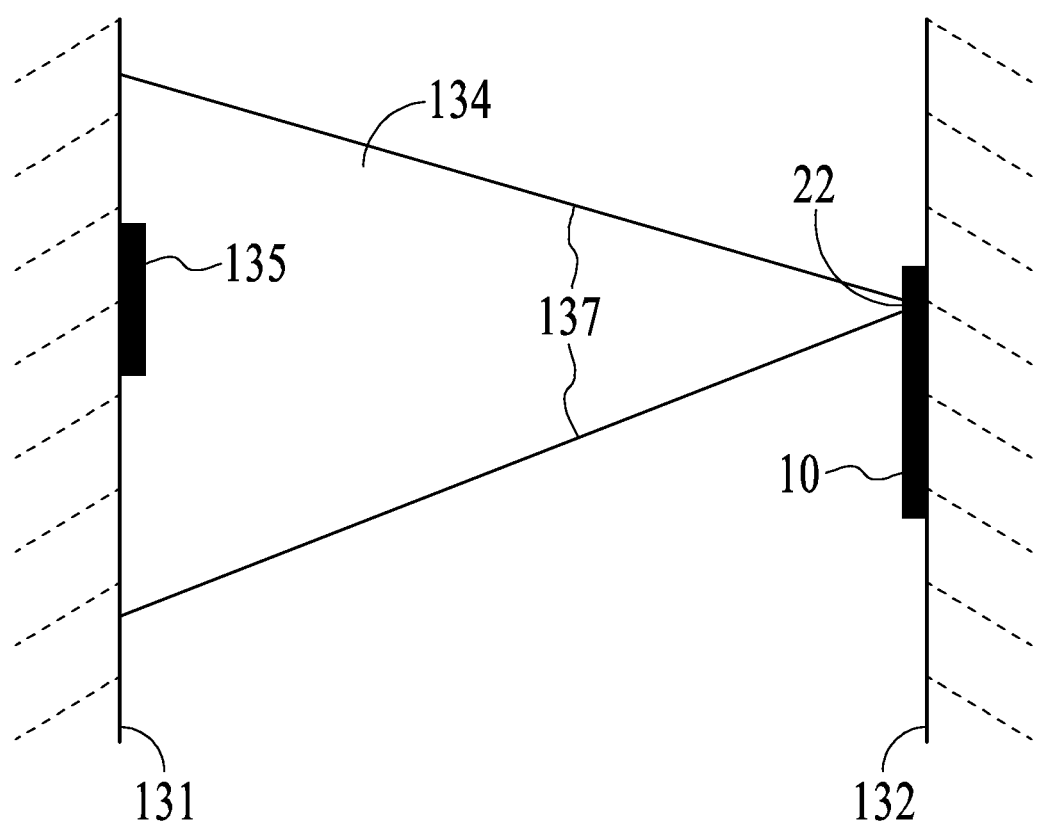
FIG. 13 shows a smart mobile device used to make a calibrated measurement of the distance between two walls in accordance with an implementation.

FIG. 13 shows smart mobile device 10 used to make a calibrated measurement of the distance between a wall 131 and a wall 132. Lines 137 define a field of view 134 for back facing camera 22. A case 135 is attached to wall 131. Case 135 includes a calibration pattern that faces towards wall 132.

Figure 14:
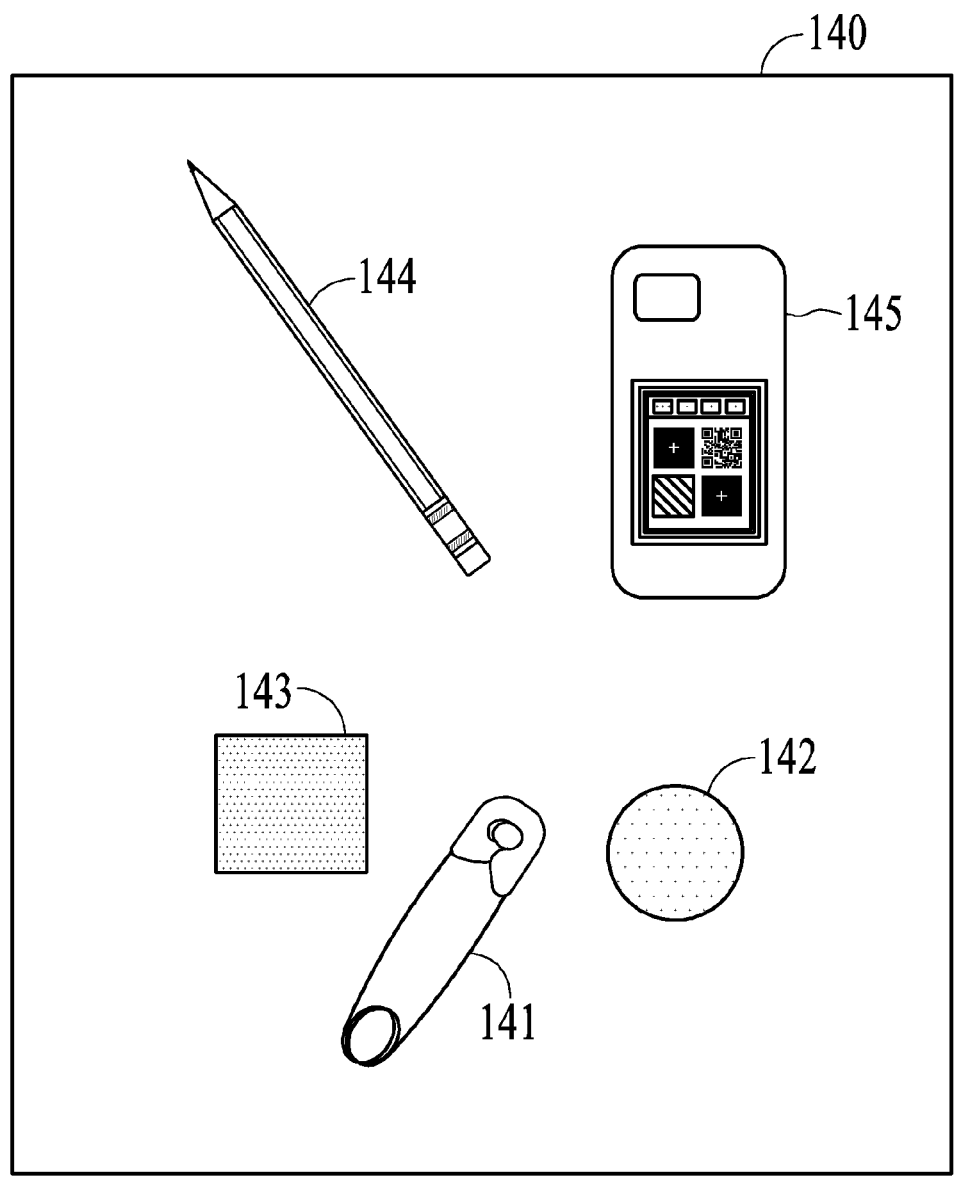
FIG. 14 shows a simplified example of an image that includes a case for a smart mobile device used as a calibration target useful when making measurements on other objects within the image in accordance with an implementation.

FIG. 14 shows a simplified example of a recorded image 140 that includes an image of case 145 with an embedded calibration pattern. The calibration can be used for measurements of dimensions, colorimetery, brightness and so on of other objects within recorded image 140. The other objects, include, for example, a safety pin 141, a pencil 144, a circular object 142 and a square object 143.

In order to activate app 23 within smart mobile device 10, app 23 needs to be transferred to smart mobile device 10 if not installed when smart mobile device 10 is purchased. For example, app 23 can be downloaded from the internet or from an app store. Also a case with an embedded calibration pattern can be obtained.

The camera setting of smart mobile device 10 will need to be set according to any instructions included with app 23.

The calibration pattern may then be included in the field of view of a camera of smart mobile device 10. For example, a particular background may be specified or suggested to maximize contrast between the calibration pattern and the background The camera of smart mobile device 10 is focused on the calibration pattern based on the capability of the camera of smart mobile device 10. The focus capability may be, for example, auto focus, tap to focus, or another focusing capability. Once in focus, an image is captured.

App 23 will analyze the captured image. For example, if the captured image has a two-dimensional bar code, app 23 will read and decode the two-dimensional bar code and act in accordance with the encoded instructions. If the two-dimensional bar code includes a calibration code identifying indicia and all calibration information, then the app 23 will decode the information, associate the information with the identifying indicia of the calibration pattern and store the information in the memory of smart mobile device 10. The information can in the future be accessed based on the associated identifying indicia. Alternatively, if the two-dimensional bar code does not include all available information about the calibration pattern, app 23 can use the identifying indicia, for example, to access information about the calibration pattern previously stored in smart mobile device 10 or download additional information about the calibration pattern from an App central server (cloud) when smart mobile device 10 is connected to the Internet. For example, once information about the calibration pattern is stored in smart mobile device 10, the setup procedure of app 23 will prompt user for registering this specific calibration pattern with smart mobile device 10. If permission is granted, registration will proceed.

FIG. 3 illustrates the process of measuring object 36 in field of view 33 of back facing camera 22. In a first step, calibration target 35 is placed within field of view 33, preferably in focus plane 34 of measuring object 36. For example, as described above, calibration target 35 is a calibration pattern on a case of smart mobile phone 10. Smart mobile phone 10 is removed from the case and the case placed so that that calibration pattern plane is parallel to the measurement plane of object 35 and any other objects to be measured. Smart mobile phone 10 is positioned so that object 35, and any other objects to be measured, are maximized within field of view 33. For example, FIG. 14 shows multiple images within field of view 33.

In a third step, back facing camera 22 is focused at focus plane 34 and an image captured. For example, a manual focus or an auto focus capability, such as a tap-on-focus, is used to focus camera lens 31 on calibration target 35.

Once an image is captured, app 23 analyzes the capture image to perform a calibration process. Particularly, app 23 analyzes the captured image to determine an exact location and orientation of calibration target 35. App 23 will also look for a two-dimensional bar code or other source of encoded information within the captured image. From information obtained from, for example, a two-dimensional bar code or other source of encoded information, app 23 will verify smart mobile device 10 has access to the relevant calibration information associated with calibration target 35 and if so, use the relevant calibration information associated with calibration target 35 for calibrating back facing camera 22. If smart mobile device 10 does not have access to the relevant calibration information associated with calibration target 35, app 23 will try to obtain access to this information, for example, by connecting user to an online source where access can be obtained.

Once app 23 has access to relevant calibration information, app 23 uses algorithms that use geometrical patterns included within the calibration pattern the and their geometrical relationships to calculated measurement values, as is understood in the art.

In a fourth step, object 36 is measured. To measure object 36, the user brings up the calibrated captured image. The calibrated captured image will have calibration information with it. The calibrated captured image can be viewed and processed on smart mobile device 10 or transferred to another computing device such as a personal computer for viewing and measuring. For example, an object measurement menu bar is presented to use for making the measurement process more convenient. At the user's option, various measurements can be made. For example, a point to point measurement can be made using a ruler placement Also, an area measurement can be made by placing a geometrical shape on an object. Various associated measurements such as dimensions, gray level, density, colorimitery, and so on can be calculated.

Alternatively, a user can identify an object and automated object recognition could be performed. The automated object recognition could return detected values for various associated measurements such as dimensions, gray level, density, colorimetery.

Alternatively, app 23 can be written so that when run on mobile device 10 mobile device 10 creates a process running on mobile device 10 that can detect a case that does not necessarily include a calibration pattern. For example, the case can be detected by detecting the outline of the case or some prominent feature on the case or pattern on the case. In this example, app 23 uses stored information about the case to make a calibrated measurement. For example, the stored information can be dimensional information, brightness information, color information or information about a feature or a pattern on the case.

FIG. 13 illustrates measurement of distance between two objects, in this case the distance between wall 131 and wall 132. In a first step, the calibration target, i.e., case 135 with an embedded calibration pattern, is placed on the first object, i.e., wall 131.

In a second step, smart mobile device 10 is placed on the second object, i.e., wall 132. Smart mobile device 10 is mounted on wall 132 so that camera 22 is directly facing in a direction perpendicular to case 135 (the calibration target).

In a third step, the zoom of camera 22 is adjusted to maximize the size of the calibration target in field of view 137 of smart mobile device 10.

In a fourth step, camera 22 is focused on case 135 and an image captured. For example, a manual focus or an auto focus capability, such as a tap-on-focus is used to focus camera lens 31 on case 135.

In a fifth step, once an image is captured, app 23 analyzes the capture image to perform a calibration process. Particularly, app 23 analyzes the captured image to determine an exact location and orientation of case 135. App 23 will also look for a two-dimensional bar code or other source of encoded information within the captured image. From information obtained from, for example, a two-dimensional bar code or other source of encoded information, app 23 will verify smart mobile device 10 has access to the relevant calibration information associated with the calibration pattern embedded on case 135 and if so, use the relevant calibration information associated with the calibration pattern embedded on case 135 for calibrating back facing camera 22. If smart mobile device 10 does not have access to the relevant calibration information associated with calibration target 35, app 23 will try to obtain access to this information, for example, by connecting user to an online source where access can be obtained.

Once app 23 has access to relevant calibration information, app 23 uses algorithms that use specific patterns in the calibration pattern designed for distance measurement through triangulation.

Figure 15:
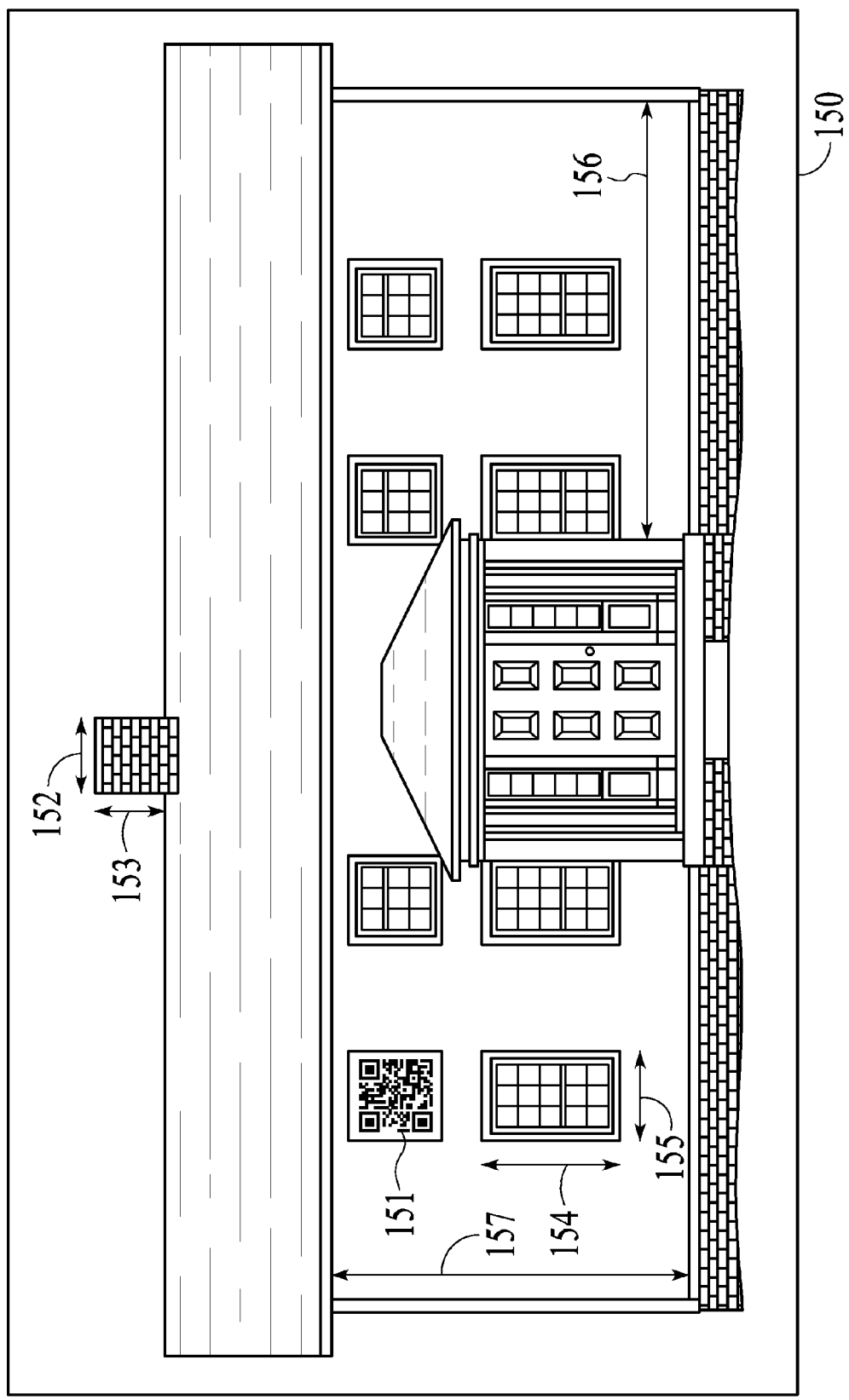
FIG. 15 shows a simplified example of an image that shows a house on which has been mounted a calibration pattern in a window in accordance with an implementation.

A calibration pattern within an image can be used apart from a smart mobile device. For example, FIG. 15 shows a simplified example of an image 150 that shows a house 157 on which has been mounted a calibration pattern 151 in a window of the house. For example the image is a digital image captured with any digital camera. The image can be displayed on any computer system able to display digital images. Calibration pattern 151 contains information about calibration pattern 151. For example calibration pattern 151 is a two-dimensional bar code that contains encoded display information about calibration pattern 151.

The information displayed in calibration pattern 151 is utilized to make one or more calibrated measurements, such as those represented by an arrow 152, an arrow 153, an arrow 154, an arrow 155, and an arrow 156. The calibrated measurements are utilized, for example, by a computing system used by a user, or by a remote server accessed by a user.

The inclusion of a calibration pattern in a digital image allows for a computer system to make calibrated measurements. For example, the image can contain objects of any size. The calibrated measurements can be made by any computing system with sufficient processing power to make the pertinent calculations.

The information displayed in a calibration pattern can also be used to validate user permission to use a particular application to make calibrated measurements. For example, a particular calibration application can be set up to only operate on images that display a particular calibration pattern or group of calibration patterns. For example, each calibration pattern may include a serial number or some other identification indicia that uniquely identifies the calibration pattern. The application making the calibration measurements can use this identification indicia as a pass code to validate user rights to use the application to make calibrated measurements.

Figure 16:
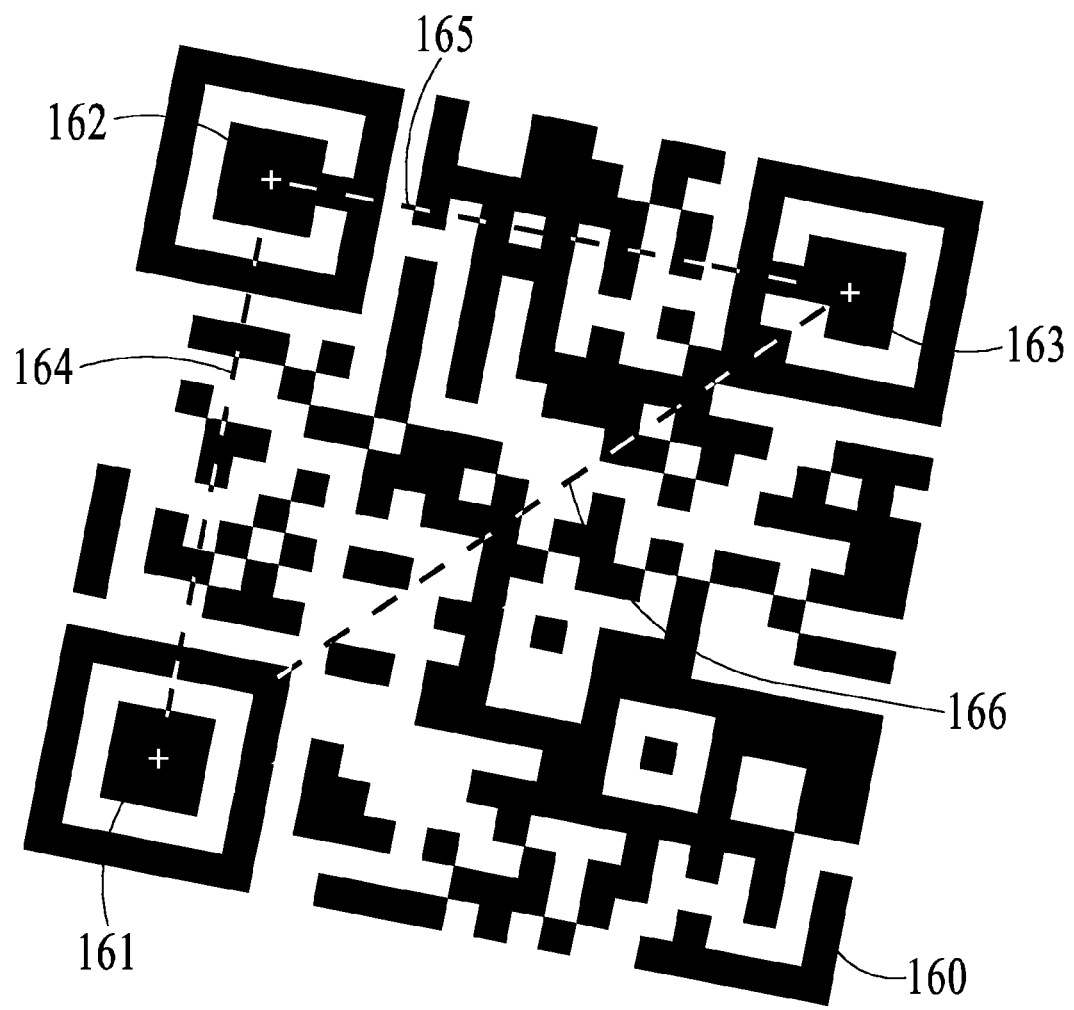
FIG. 16 shows an example of a two dimensional bar code used as a calibration pattern in accordance with an implementation.

FIG. 16 shows a two-dimensional bar code 160 used as a calibration pattern. While in FIG. 16, calibration pattern 160 is in a tilted orientation, app 23 will calculate the orientation and take the orientation into account when making calibrated measurements. For example, information about calibration pattern 160 will include a value for an actual distance, represented by a line 164, between a point 161 and a point 162, a value for an actual distance, represented by a line 165, between point 162 and a point 163 and a value for an actual distance, represented by a line 166, between point 163 and point 161. Within calibration pattern 160, a high gradient pattern can be inserted to be used to sharpen image focus. Also particular color or grey areas can be added to calibration pattern 160 to allow for calibration of color and/or brightness for a captured image that includes calibration pattern 160.

As illustrated in FIG. 3, placing camera 22 and calibration target 35 in parallel planes when capturing an image of calibration target 35 is important to achieve accurate measurements. Since a user may hold mobile device 10 in hand when capturing an image, there may be some variance from the ideal positioning of camera 22 and calibration target 35 in parallel planes. To accommodate this lack of precision, four or more measuring points of calibration target can be used to measure co-planarity of the planes in which camera 22 and calibration target 35 are situated.

Figure 17:
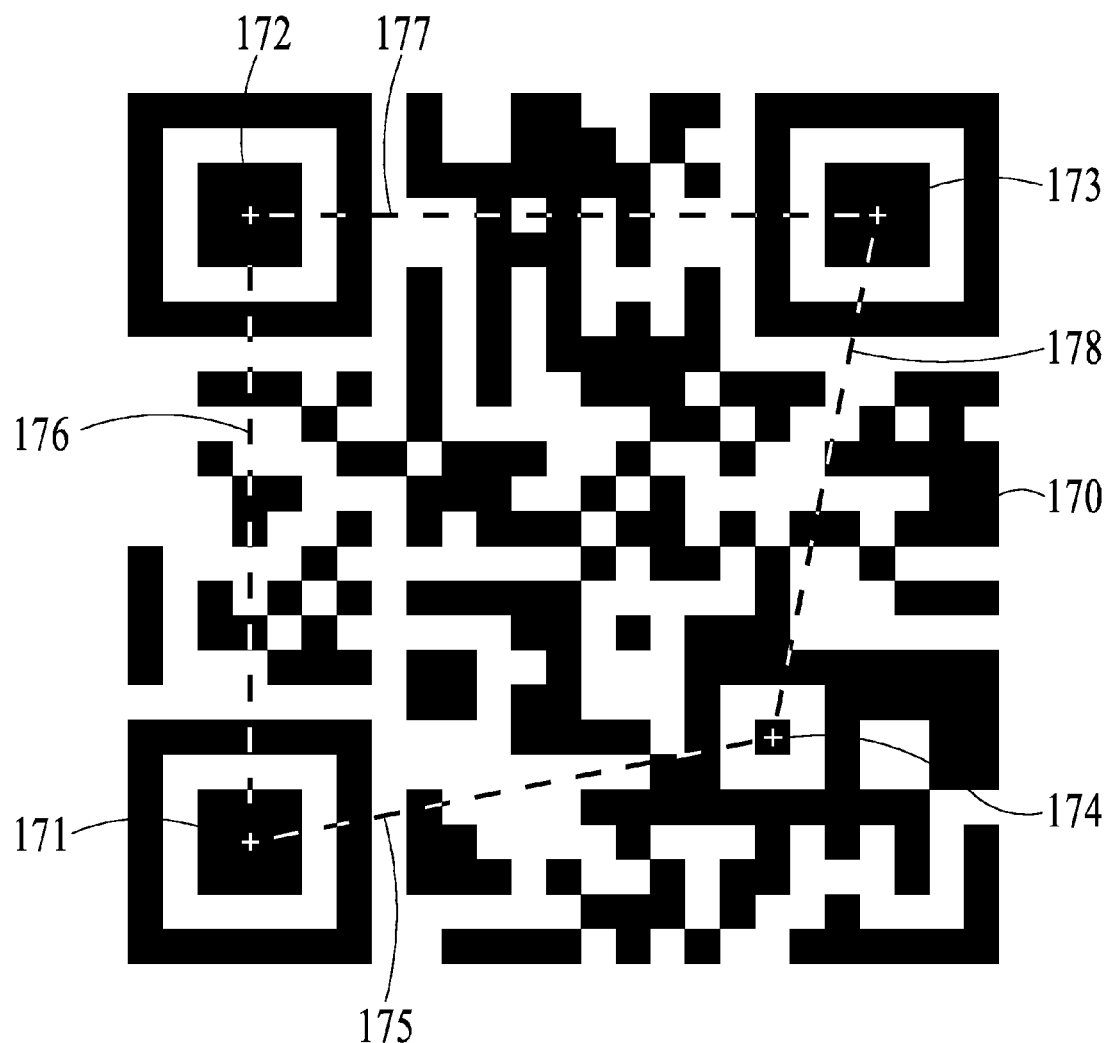
FIG. 17 shows another example of a two dimensional bar code used as a calibration pattern in accordance with an implementation.

For example, FIG. 17 shows a two-dimensional bar code 170 used as a calibration pattern. For example, information about calibration pattern 170 will include a value for an actual distance, represented by a line 176, between a point 171 and a point 172, a value for an actual distance, represented by a line 177, between point 172 and a point 173, a value for an actual distance, represented by a line 178, between point 173 and a point 174, and a value for an actual distance, represented by a line 175, between point 174 and point 171.

Points 171, 172 and 173 are used for geometrical calibration of the captured image and orientation assessment of the calibration pattern. All four points 171, 172, 173 and 174 are used for a co-planarity measurement. The image co-planarity measurement will have multiple applicability. That is, the co-planarity measurement is used to access image co-planarity at the time of the image capture and provides real-time feedback to the user of smart mobile device 10 on the parallelism of the camera with the calibration pattern image plane when the user is about to capture an image. For example, visual and/or audio feedback is given to the user when the camera with the calibration pattern are co-planar or alternatively when the camera with the calibration pattern are not co-planar.

Once an image is captured the co-planarity measurement is used to correction any deviation from co-planarity between the camera the calibration pattern image plane. The co-planarity measurement can also be used as a factor in calculating and presenting to the user a value that indicates an expected accuracy of the calibrated measurement.

While app 23 within mobile server 10 utilizes the calibration pattern to make calibrated measurements, such calibrated measurements could also be done by any computer implemented system that includes a processor and computer readable medium encoded with processor readable instructions that, when read, implement a process on the processor that can detect a calibration pattern within an image where the process uses information displayed within the calibration pattern to make a calibrated measurement.

For example, a server can make a measurement by accessing a digital image, where the digital image includes a calibration pattern and the calibration pattern includes displayed information about the calibration pattern. The server reads the displayed information to obtain the information about the calibration pattern. Then the server utilizes the displayed information to make a calibrated measurement.

It is also possible to calibrate an image once and use extracted calibration information from the image to calibrate other images captured using the same image set-up (e.g., camera position, object location, lighting, etc.) To achieve this, one can calibrate the image at the time of picture taking by placing a calibration pattern in the scene and taking a picture. The calibration pattern can then be used to extract camera information about the image, which will be equally applicable to all other images subsequently captured using the same image set-up.

Figure 18:
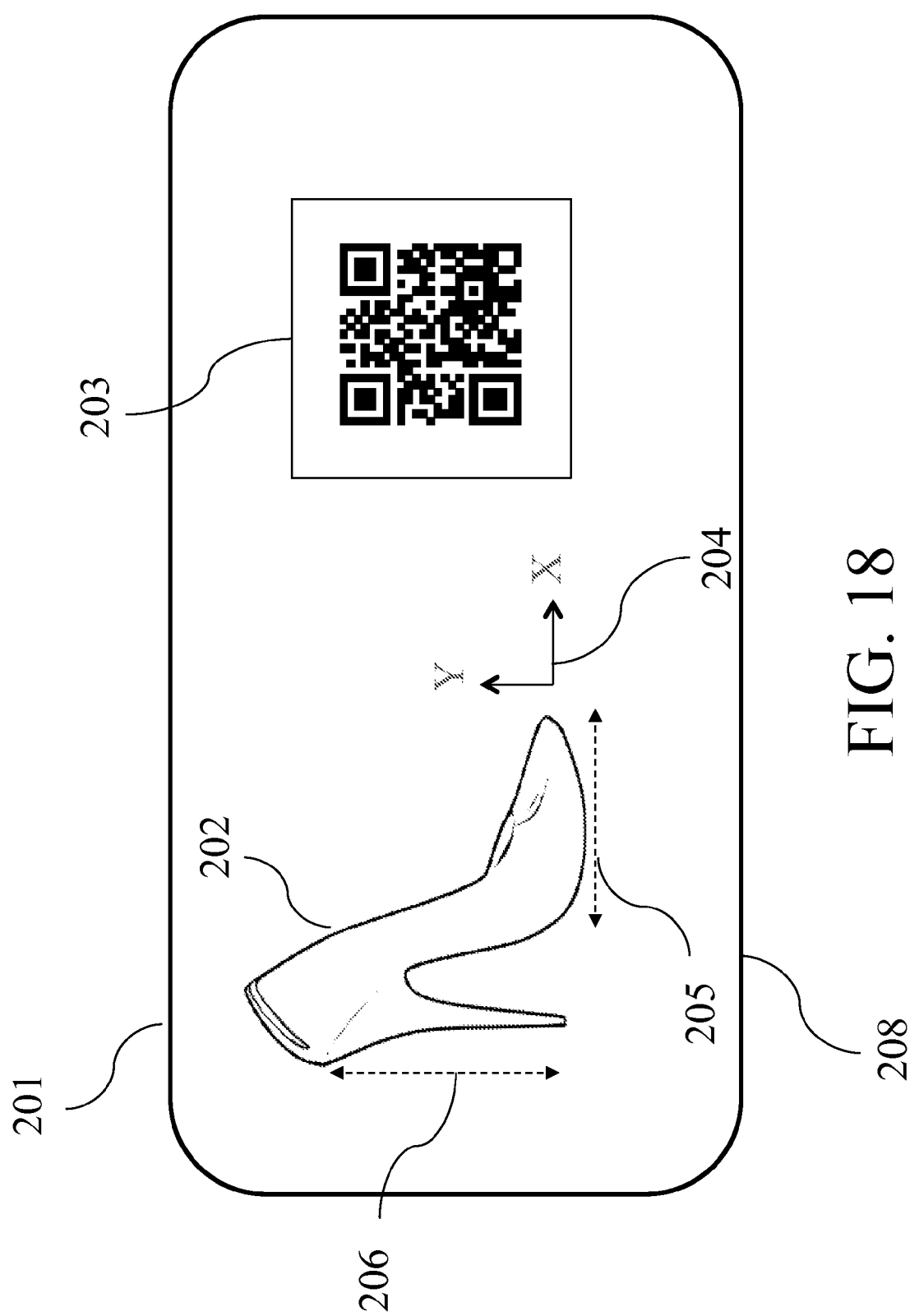
FIG. 18, FIG. 19 and FIG. 20 illustrate a calibration pattern being used to extract camera information about an image that is applicable to other images using a same image set-up in accordance with an embodiment.
Figure 19:
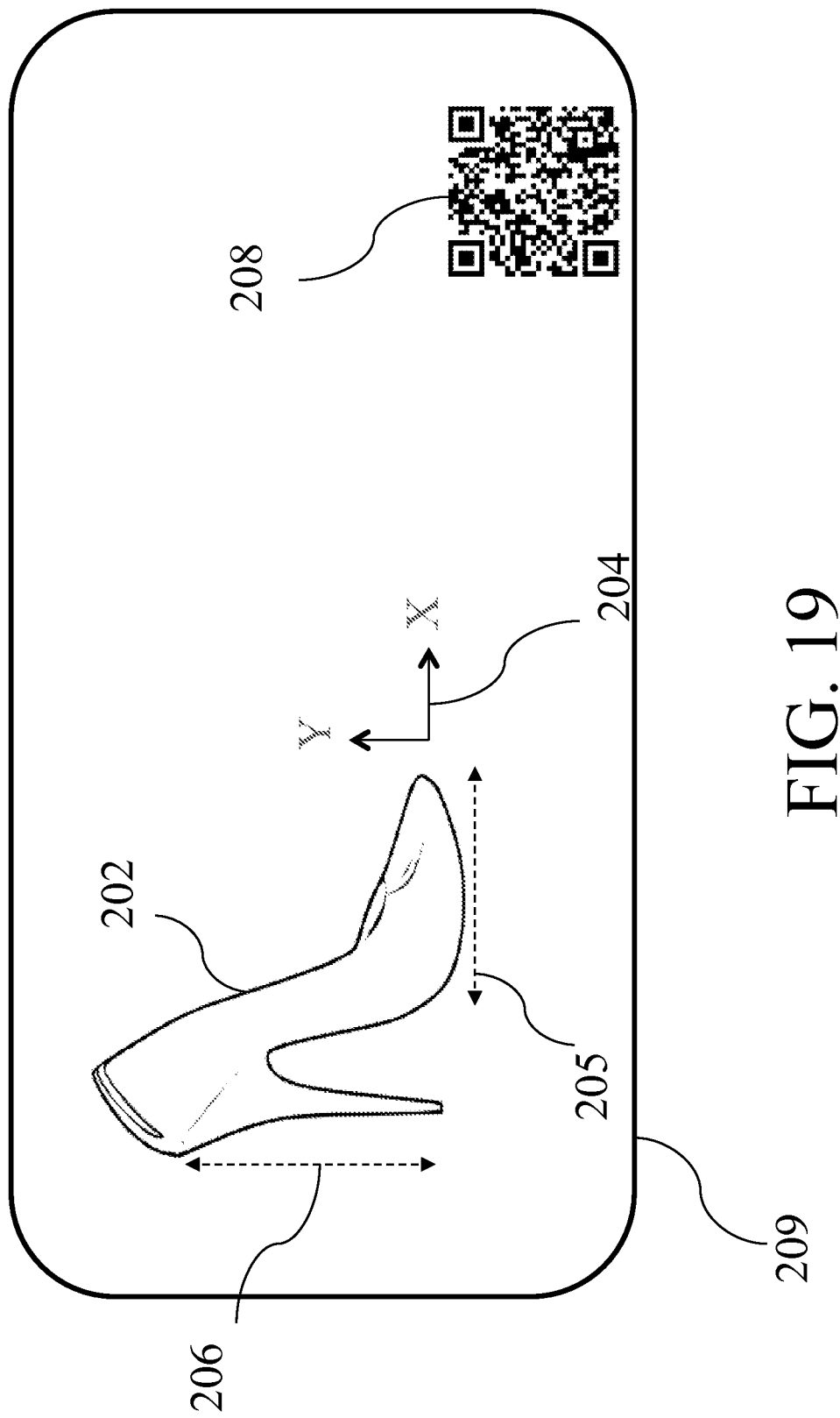
Figure 20:
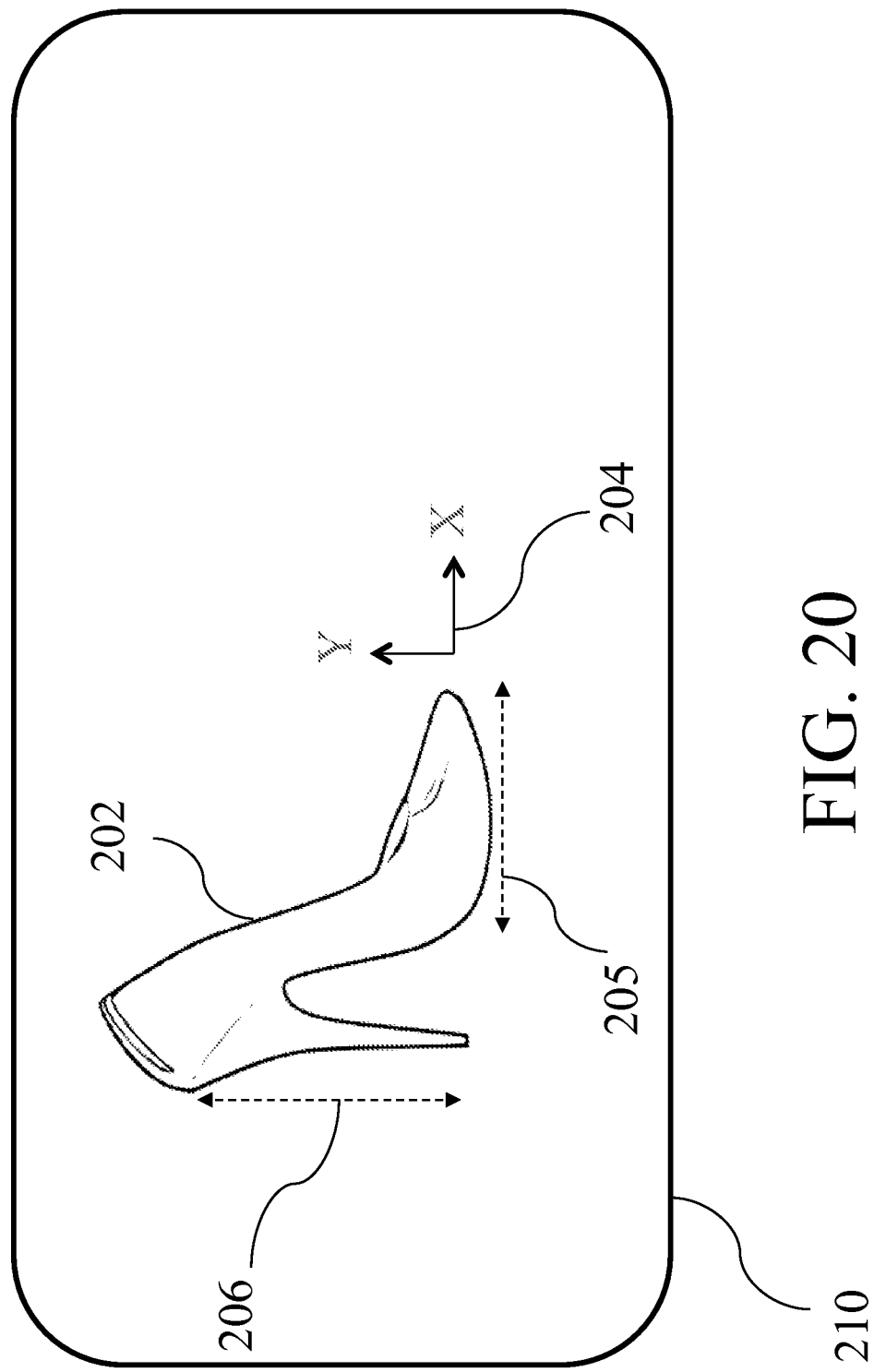

This is illustrated by FIG. 18, FIG. 19 and FIG. 20. FIG. 18 shows a shoe 202 within a picture frame 201. Also within the picture frame is media 203 that includes a calibration pattern. The calibration pattern allows for calibration of dimensions such as represented by dimensional measurements 205 and 206 and by axis of orientation 204, which are not visible in the image, but represent information available from the calibration pattern.

The calibration pattern can provide, for example, information such as pixel size in X direction, pixel size in Y direction, distance to the focus plane, location of the focus plane in the image (can be exposed with placing a graphics overlay to define this plane), if there are multiple focus plane of calibration the above attributed could be duplicated for each plane, dimensional measurement info and overlays for premeasured objects, colorimetric calibration information, brightness calibration information, capture time lighting information (flash, sunlight, etc.), scale with respect to real life (example: scale of a architectural drawing for an image of the drawing), camera settings, and so on. To define a plane of focus, a coordinate crosshair cal also be superimposed into a picture, as a guide for a user making measurements The image captured with the calibration pattern is processed to extract the calibration information. This calibration information will be the same for all subsequent images taken from the same image set-up. This allows the subsequent images to be calibrated without physically including in the image media 203 with the calibration pattern.

When a subsequent image has been taken without including in the image the calibration pattern, the calibration information can be added subsequently to the image. This could be done by visually superimposing a visible pattern containing the information onto the image or it can be done in a way that does not affect the image, for example, by including the calibration in metadata stored as part of the image. What is meant by "image metadata" herein is information stored with an image that gives information about the image but does not affect the appearance of the image as reproduced.

FIG. 19 represents the case where an image has been retaken from the same image set-up (but without media 203 in the picture). In this case the image included only shoe 202. Using calibration from the previously taken image allows for calibration of dimensions such as represented by dimensional measurements 205 and 206 and by axis of orientation 204, which are not visible in the image, but represent information available from the calibration information from the earlier taken image. The calibration information, while not originally part of the image, has been added to the image shown in FIG. 19 by superimposing a two-dimensional bar code 208 on the image shown in FIG. 19. Use of a two-dimensional bar code is only illustrative as this information could be visibly included on the image in other ways, for example through a one-dimensional bar code, a digitally coded label, an alphanumeric coded label or some other communication methodology visible on an image.

FIG. 20 represents another case where an image has been retaken from the same image set-up (but without media 203 in the picture). In this case the image included only shoe 202. Using calibration from the previously taken image allows for calibration of dimensions such as represented by dimensional measurements 205 and 206 and by axis of orientation 204, which are not visible in the image, but represent information available from the calibration information from the earlier taken image. The calibration information, while not originally part of the image, has been added to the image metadata, but not added to the image data. This, as shown in FIG. 20 no calibration information appears in the image itself. The calibration information is included only as part of image metadata stored with an image.

Alternative to retaking a picture with the same image set-up, the original image itself can be altered (e.g., using image processing software) to remove the calibration pattern from the original image. The calibration information could then be re-added to the image in another form, for example, by superimposing the image back onto the image, as illustrated in FIG. 19, or by including the calibration information in image metadata stored with the image, as illustrated by FIG. 20.

The ability to extract calibration information from a first taken image and reuse the calibration information in subsequent images taken with the same image set-up can be advantageous. For example, volume manufactures may want to develop a picture taking setup where a camera and picture are calibrated once and images of different objects are taken for future at will measurements. A shoe manufacturer, for example, may make a picture taking setup and calibrate the system via a calibration pattern or other means and maintain this setup to take pictures of multiple shoes placed in the focus plane.

The ability to extract calibration information from a first taken image and then in post image processing removing the image from the original image allows inclusion of the calibration information, for example in image metadata for the image, while maintaining image originality, artistic perspective and cleanliness. Any calibration pattern in the image that distracts the viewer and impacts the artistic perspective of the image is removed.

Sometimes it may be necessary to alter calibration information stored with an image. For example, for an original image taken with a calibration pattern, resolution, or some other feature of the image set-up may vary from subsequent images captured without the calibration pattern or even the images directly derived from an original image. This may occur, for example, where an image taken at a high resolution is uploaded to an on-line site that limits the resolution of uploaded images. If the calibration information stored with the original image (either visible on the picture on in image metadata), is based on the higher resolution, the calibration information stored with the image needs to be resolution scaled to be accurate. If the resolution scaling information of the original image is included in the calibration data, this allows the change in resolution to be taken into account when subsequently interpreted. Including such information, either visibly or with image metadata for the image, allows for precise interpretation of measurement information.

The foregoing discussion discloses and describes merely exemplary methods and implementations. As will be understood by those familiar with the art, the disclosed subject matter may be embodied in other specific forms without departing from the spirit or characteristics thereof. Accordingly, the present disclosure is intended to be illustrative, but not limiting, of the scope of the invention, which is set forth in the following claims.

What is claimed is:

1. A method comprising:
   (a) capturing a digital image that includes both a physical object and a calibration pattern, said calibration pattern including displayed information about said calibration pattern, where said calibration pattern and said physical object are non-overlapping with one another in said digital image;
   (b) reading, from said captured digital image that includes both said physical object and said calibration pattern, said displayed information about said calibration pattern to determine calibration information pertaining to said physical object;
   (c) generating a new image of said physical object, said new image not including said calibration pattern;

(d) adding said calibration information to said new image;

(e) wherein said calibration information is said added to said new image by including said calibration information as metadata for said new image within an image file containing said new image;

(f) wherein said calibration information includes resolution scaling information;

(g) capturing another digital image that includes both another physical object and another calibration pattern, said another calibration pattern including another displayed information about said another calibration pattern, where said another calibration pattern and said another physical object are non-overlapping with one another in said another digital image;

(h) reading, from said another captured digital image that includes both said another physical object and said another calibration pattern, said another displayed information about said another calibration pattern to determine another calibration information pertaining to said another physical object;

(i) generating another new image of said another physical object, said another new image not including said another calibration pattern;

(j) adding said another calibration information to said another new image.

2. The method of claim 1 wherein said another calibration information is said added to said another new image by including said another calibration information as metadata for said another new image within another image file containing said another new image.

3. The method of claim 2 wherein said another calibration information includes another resolution scaling information.

4. The method of claim 3 further comprising:
(a) displaying said new image on a display based upon said resolution scaling information said added to said new image;
(b) simultaneously displaying said another new image on said display based upon said another resolution scaling information said added to said another new image;
(c) where said resolution scaling information is different than said another resolution scaling information.

* * * * *

UNITED STATES PATENT AND TRADEMARK OFFICE
CERTIFICATE OF CORRECTION

| | | |
|---|---|---|
| PATENT NO. | : 9,672,623 B2 | Page 1 of 2 |
| APPLICATION NO. | : 13/791987 | |
| DATED | : June 6, 2017 | |
| INVENTOR(S) | : Mansoor Ghazizadeh | |

It is certified that error appears in the above-identified patent and that said Letters Patent is hereby corrected as shown below:

In the Specification

Column 5, Line 8:
Change "to that could be" to read --so that it could be--;

Column 5, Line 10:
Change "integrated" to read --integrating--;

Column 5, Line 44:
Change "in calibration" to read --in a calibration--.

Column 6, Line 7:
Change "take" to read --takes--;

Column 6, Line 10:
After "view" insert a --.--.

Column 7, Line 3:
After "background" insert a --.--.

Column 8, Line 1:
Change "calibration pattern the and" to read --calibration pattern and--;

Column 8, Line 14:
After "placement" insert a --.--.

Column 10, Line 28:
Change "correction" to read --correct--;

Signed and Sealed this
Twentieth Day of February, 2018

Andrei Iancu
*Director of the United States Patent and Trademark Office*

CERTIFICATE OF CORRECTION (continued)
U.S. Pat. No. 9,672,623 B2

Column 10, Line 29:
Change "the camera the" to read --the camera and the--.

Column 11, Line 5:
Change "multiple focus plane" to read --multiple focus planes--;

Column 11, Line 11:
Change "scale of a" to read --scale of an--;

Column 11, Line 13:
Change "crosshair cal" to read --crosshair can--;

Column 11, Line 14:
After "measurements" insert a --.--;

Column 11, Line 20:
Delete "in".

Column 12, Line 35:
Change "picture on" to read --picture or--.